(12) United States Patent
Mueller et al.

(10) Patent No.: US 11,534,124 B2
(45) Date of Patent: Dec. 27, 2022

(54) SYSTEM WITH A GANTRY OF A COMPUTED TOMOGRAPHY DEVICE AND A DOCKING STATION AND METHOD FOR COOLING A COMPONENT OF THE GANTRY

(71) Applicant: Siemens Healthcare GmbH, Erlangen (DE)

(72) Inventors: Hans-Juergen Mueller, Pretzfeld (DE); Christoph Dickmann, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 25 days.

(21) Appl. No.: 17/238,520

(22) Filed: Apr. 23, 2021

(65) Prior Publication Data

US 2021/0236076 A1    Aug. 5, 2021

Related U.S. Application Data

(62) Division of application No. 16/575,896, filed on Sep. 19, 2019, now Pat. No. 11,000,246.

(30) Foreign Application Priority Data

Sep. 28, 2018 (DE) ...................... 10 2018 216 751.6

(51) Int. Cl.
*A61B 6/03* (2006.01)
*A61B 6/00* (2006.01)

(52) U.S. Cl.
CPC ............ *A61B 6/4488* (2013.01); *A61B 6/035* (2013.01); *A61B 6/4405* (2013.01); *A61B 6/4429* (2013.01)

(58) Field of Classification Search
None
See application file for complete search history.

(56) References Cited

U.S. PATENT DOCUMENTS

| | | |
|---|---|---|
| 4,752,310 A | 6/1988 | Maier-Laxhuber et al. |
| 6,412,979 B1 | 7/2002 | Hell et al. |
| | (Continued) | |

FOREIGN PATENT DOCUMENTS

| | | | |
|---|---|---|---|
| CN | 114098776 A | * 3/2022 | ............. A61B 6/032 |
| DE | 102012213875 A1 | 2/2014 | |
| DE | 102016208123 A1 | 9/2017 | |

OTHER PUBLICATIONS

Extended German Search Report for DE Application No. 102018216751, dated May 23, 2019.
(Continued)

*Primary Examiner* — Thomas R Artman
(74) *Attorney, Agent, or Firm* — Harness, Dickey & Pierce, P.L.C.

(57) ABSTRACT

A system with a gantry of a computed tomography device and a docking station and method are for cooling a component of the gantry. In an embodiment, the system includes a gantry of a computed tomography device, the gantry including a chassis and a heat store; and a docking station. The gantry is movable via the chassis relative to the docking station. The gantry and the docking station are detachably connectable to one another such that a detachable coolant-exchange connection for exchanging a coolant and/or a detachable heat-conduction connection for heat conduction is formed between the heat store and the docking station.

30 Claims, 11 Drawing Sheets

(56) References Cited

U.S. PATENT DOCUMENTS

| | | | |
|---|---|---|---|
| 7,499,524 B2 | 3/2009 | Anderton et al. | |
| 8,690,745 B2 | 4/2014 | Rozas et al. | |
| 9,161,731 B2 * | 10/2015 | Foerner | A61B 6/032 |
| 10,792,001 B2 * | 10/2020 | Hoernig | A61B 6/4405 |
| 11,000,246 B2 * | 5/2021 | Mueller | A61B 6/4405 |
| 2005/0117706 A1 | 6/2005 | Powell | |
| 2007/0253540 A1 | 11/2007 | Anderton et al. | |
| 2011/0124946 A1 | 5/2011 | Rozas et al. | |
| 2014/0037071 A1 | 2/2014 | Foerner et al. | |
| 2017/0325763 A1 | 11/2017 | Hoernig et al. | |
| 2020/0100742 A1 | 4/2020 | Mueller et al. | |
| 2021/0236076 A1 * | 8/2021 | Mueller | A61B 6/4405 |
| 2022/0061789 A1 * | 3/2022 | Dickmann | A61B 6/4405 |

OTHER PUBLICATIONS

Non-Final Office Action dated Sep. 10, 2010 in U.S. Appl. No. 16/575,896.

Notice of Allowance dated Jan. 13, 2021 in U.S. Appl. No. 16/575,896.

* cited by examiner

SYSTEM WITH A GANTRY OF A COMPUTED TOMOGRAPHY DEVICE AND A DOCKING STATION AND METHOD FOR COOLING A COMPONENT OF THE GANTRY

CROSS-REFERENCE TO RELATED APPLICATIONS

The present application is a Divisional of, and claims priority under 35 U.S.C. §§ 120 and 121 to, U.S. application Ser. No. 16/575,896, filed on Sep. 19, 2019, which claims priority under 35 U.S.C. § 119 to German patent application number DE 102018216751.6 filed Sep. 28, 2018, the entire contents of each of which are incorporated herein by reference.

FIELD

Embodiments of the invention generally relate to a system with a gantry of a computed tomography device and a docking station and a method for cooling a component of the gantry.

BACKGROUND

A computed tomography device with a mobile gantry can in particular be used in hygienically sensitive areas, for example in operating rooms. As far as possible in the hygienically sensitive areas it is in particular necessary to avoid cooling of the gantry which is substantially based on heated air flowing out of the gantry into the examination room. In addition, both the cooling and the electrical energy supply for the mobile gantry should be embodied such that, independently of electrical terminals, it is possible to acquire as many items of projection data as possible without this entailing any significant impairment of the quality of the projection data.

SUMMARY

At least one embodiment of the invention provides improved cooling of a mobile gantry of a computed tomography device. The claims relate to further advantageous embodiments and aspects of the invention.

At least one embodiment of the invention relates to a system comprising:
a gantry of a computed tomography device, wherein the gantry comprises a chassis and a heat store; and
a docking station,
the gantry being movable via the chassis relative to the docking station, and the gantry and the docking station being connectable, and in particular are connected, detachably to one another such that a detachable coolant-exchange connection for exchanging a coolant and/or a coolant reservoir and/or a detachable heat-conduction connection for heat conduction is formed between the heat store and the docking station.

At least one embodiment of the invention further relates to a system comprising:
a gantry of a computed tomography device, the gantry including a chassis and a heat store; and
a docking station,
the gantry being movable, via the chassis, relative to the docking station, and
the gantry and the docking station being detachably connectable such that at least one of a detachable coolant-exchange connection for exchanging a coolant, a coolant reservoir and a detachable heat-conduction connection for heat conduction is formed between the heat store and the docking station.

At least one embodiment of the invention further relates to a method for cooling a component of a gantry of a computed tomography device, wherein the method includes:
cooling the component of the gantry, wherein heat is received in a heat store, which is integrated in the gantry,
moving the gantry via a chassis relative to a docking station,
connecting the gantry and the docking station detachably to one another such that a detachable coolant-exchange connection for exchanging a coolant and/or a coolant reservoir and/or a detachable heat-conduction connection for heat conduction is formed between the heat store and the docking station.

At least one embodiment of the invention further relates to a method for cooling a component of a gantry of a computed tomography device, the method comprising:
cooling the component of the gantry, wherein heat is received in a heat store integrated in the gantry;
moving the gantry, via a chassis, relative to a docking station; and
connecting the gantry and the docking station, detachably, such that a detachable coolant-exchange connection, for at least one of exchanging a coolant, a coolant reservoir, and a detachable heat-conduction connection for heat conduction, is formed between the heat store and the docking station.

BRIEF DESCRIPTION OF THE DRAWINGS

The following describes the invention with reference to the example embodiments and with reference to the appended figures. The depiction in the figures is schematic, greatly simplified and not necessarily true to scale.

The figures show.

DETAILED DESCRIPTION OF THE EXAMPLE EMBODIMENTS

Figure 1:
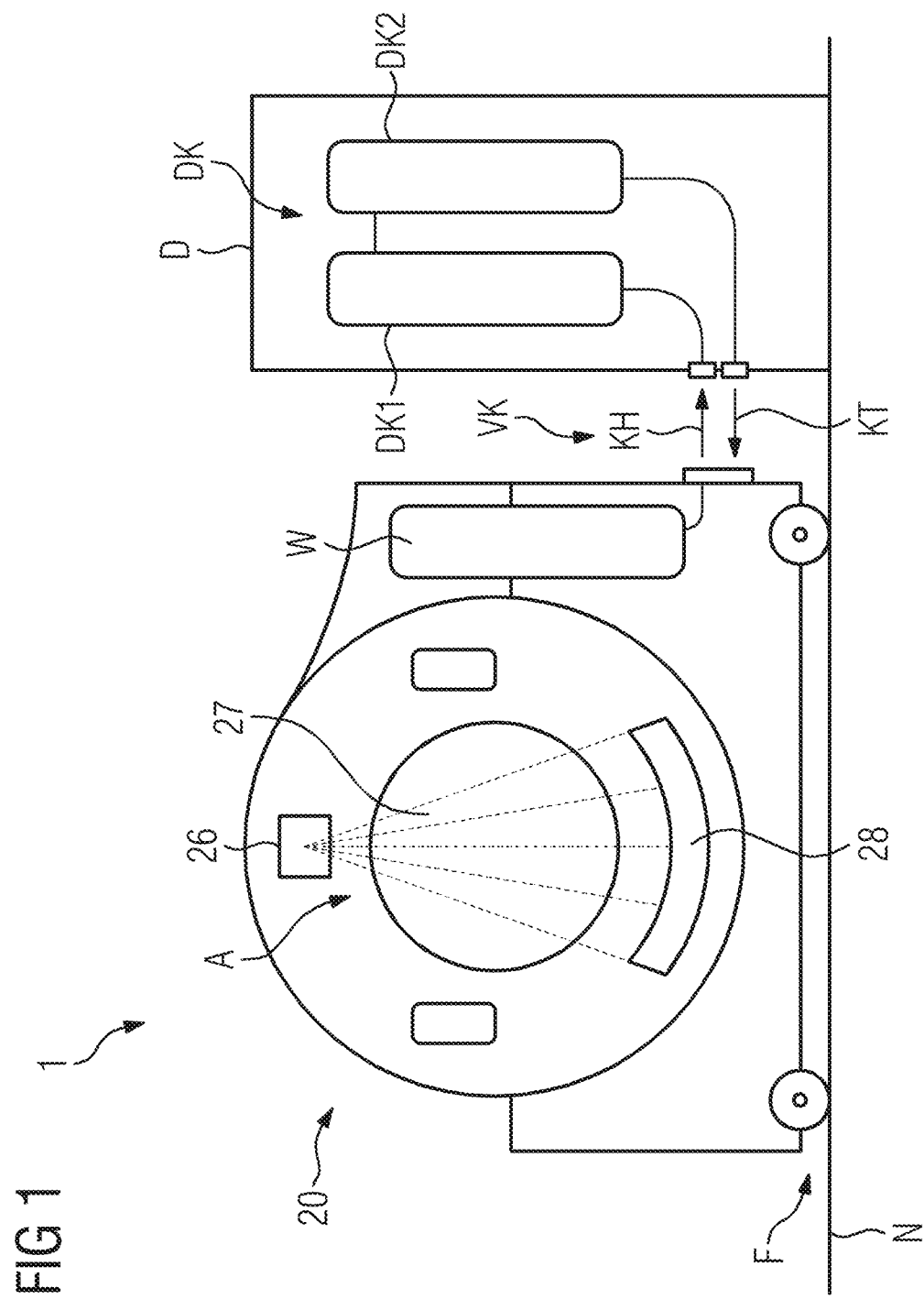
FIG. 1 a system with a coolant store and a detachable coolant-exchange connection between the gantry and the docking station, FIG. 2 a system with a coolant store, a detachable coolant-exchange connection between the gantry and the docking station and a heat sink, FIG. 3 a system with a coolant store, a detachable coolant-exchange connection between the gantry and the docking station for exchanging a coolant and a coolant reservoir, FIG. 4 a system with a latent heat store and a detachable heat-conduction connection, FIG. 5 a system with a sorption-heat store and a detachable heat-conduction connection, FIG. 6 a system with a heat store and a heat sink, wherein the gantry and the docking station are not connected via a detachable coolant-exchange connection, FIG. 7 a sequence diagram of a method for cooling a component of a gantry of a computed tomography device, FIG. 8 a system with a plurality of docking stations, which are arranged in different rooms, FIG. 9 a system with a plurality of docking stations, which are arranged in different rooms, wherein a docking station is integrated in a patient-support apparatus, FIG. 10 a system with a docking station, which is arranged in a docking-station room located between two rooms, FIG. 11 a system with a docking station, which is arranged in a docking-station room embodied as separate plant room that can only be reached via the corridor.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a system comprising:

a gantry of a computed tomography device, wherein the gantry comprises a chassis and a heat store; and a docking station, the gantry being movable via the chassis relative to the docking station, and the gantry and the docking station being connectable, and in particular are connected, detachably to one another such that a detachable coolant-exchange connection for exchanging a coolant and/or a coolant reservoir and/or a detachable heat-conduction connection for heat conduction is formed between the heat store and the docking station.

In particular, it can be provided that the gantry comprises a first coolant-exchange interface, that the docking station comprises a second coolant-exchange interface embodied as corresponding to the first heat-conduction interface and that the detachable coolant-exchange connection is formed by a connection between the first coolant-exchange interface and the second coolant-exchange interface. The first coolant-exchange interface and the second coolant-exchange interface can, for example, be embodied in the form of one or more quick couplings for the coolant exchange.

In particular, it can be provided that the gantry comprises a first heat-conduction interface, that the docking station comprises a second heat-conduction interface embodied as corresponding to the first heat-conduction interface, and that the detachable heat-conduction connection is formed by a connection between the first heat-conduction interface and the second heat-conduction interface.

The first heat-conduction interface and the second heat-conduction interface can, for example, be embodied in the form of one or more quick couplings for the heat conduction and/or in the form of one or more contact surfaces. According to one embodiment, the first heat-conduction interface and/or the second heat-conduction interface in each case comprise a thermally conductive pad. In particular, it can be provided that the detachable heat-conduction connection has a thermal conductivity of at least 300 watts, for example at least 1 kilowatt, in particular at least 3 kilowatts, in particular at least 10 kilowatts.

The quick couplings can in particular be embodied such that the corresponding interfaces are coupled to one another on an approach effected by the relative movement of the gantry relative to the docking station and/or fixed to one another by automatic locking. The quick couplings can in particular be embodied such that the corresponding interfaces are decoupled on a distancing effected by the relative movement of the gantry relative to the docking station and/or are separated from one another by the automatic cancellation of the locking.

Corresponding interfaces, for example quick couplings, can be used for an in particular bidirectional data transmission connection between the docking station and the gantry and/or for a connection for the transmission of electrical energy from the docking station to the gantry. The electrical energy transmitted from the docking station to the gantry can, for example, be used to charge a rechargeable storage device for electrical energy for the gantry, for example a battery.

The heat store can, for example, be integrated in the gantry and/or in particular embodied for the temporary intermediate storage of heat. The docking station can, for example, be permanently installed relative to an environment, wherein the gantry can be moved relative to the environment via the chassis. The docking station can in particular be connected to a water grid and/or to a power grid.

One embodiment provides that the heat store is embodied as a coolant store, wherein the docking station comprises a coolant-store region, wherein a heated coolant can be transferred from the heat store into the coolant-store region of the docking station and/or a cooled coolant can be transferred from the coolant-store region of the docking station into the heat store via the detachable coolant-exchange connection.

One embodiment provides that the heat store comprises a replaceable coolant reservoir and/or that the coolant is located in the replaceable coolant reservoir. The coolant reservoir can, for example, comprise one or more shut-off units, for example in the form of valves, in order in particular to prevent or control outflow of the coolant from the coolant reservoir and/or inflow of the coolant into the coolant reservoir.

The shut-off unit of the coolant reservoir can in particular be embodied to release and/or block a coolant flow through the shut-off unit automatically, for example based on a control signal which is received by the shut-off unit. The gantry and/or the docking station can in each case comprise an actuating mechanism for the shut-off unit, which is embodied to actuate the shut-off unit, for example based on a control signal which is received by the actuating mechanism. The actuation of the shut-off unit via the actuating mechanism can in particular effect a release and/or blocking of the coolant flow through the shut-off unit. Alternatively or additionally to the automatic control of the shut-off unit and/or the actuating mechanism, the shut-off unit and/or the actuating mechanism can be actuated manually by a user.

For example, it can be provided that the coolant reservoir in which the heated coolant is located is removed from the heat store and from the gantry, in particular pressed out and/or drawn out, and/or introduced into a coolant-store region of the docking station, in particular pressed in and/or drawn in, via a coolant-reservoir-replacing apparatus. For example, it can be provided that the coolant reservoir in which the cooled coolant is located can be removed from the coolant-store region of the docking station and from the docking station, in particular pressed out and/or drawn out, and/or introduced into the heat store, in particular pressed in and/or drawn in, via the coolant-reservoir-replacing apparatus.

To this end, the coolant-reservoir-replacing apparatus can, for example, comprise one or more pistons, one or more robot arms, one or more grippers, one or more guide elements for the coolant reservoir, in particular in the form of a shaft or a rail, or a combination thereof. It can be further provided that the gantry and the docking station can be fixed relative to one another via a detachable connection. For example, a pin can be provided on the gantry and received into a recess provided for this purpose on the docking station in positive fitting manner. This fixing can, for example, effect an exact alignment of the gantry relative to the docking station so that, for example, a coolant reservoir can be introduced into an opening provided for this purpose and/or withdrawn from an opening provided for this purpose without striking corners or edges.

In particular it can be provided that the gantry and/or the docking station in each case comprise a quick-change system, for example in the form of a turret system, for coolant reservoirs. In particular the heat store can comprise a plurality of coolant reservoirs arranged, for example, in the gantry's quick-change system.

A gantry's quick-change system can, for example, be embodied such that it is able to position a given coolant reservoir from an active position in which the coolant reservoir is connected to cooling lines of the gantry into a passive position in which the coolant reservoir is provided separate from the cooling lines of the gantry and in particular for replacement. A docking station's quick-change system can, for example, be embodied such that it can position a given coolant reservoir from an active position in which the coolant reservoir is connected to cooling lines of the docking station into a passive position in which the coolant reservoir is provided separate from the cooling lines of the docking station and in particular for replacement.

One embodiment provides that the heat store is embodied as a latent heat store, wherein the docking station comprises a cooling unit, which is embodied to cool a latent-heat-storage medium in the heat store via the detachable heat-conduction connection.

A latent heat store is able to store thermal energy in the form of a thermodynamic phase transition of a latent-heat-storage medium, for example from solid to liquid. With phase transition from the solid state to the liquid state, thermal energy is stored by virtue of enthalpy of fusion, wherein, after the complete transition of the storage medium into the liquid state, no further thermal energy can be stored. The latent-heat-storage medium then has to be returned to the solid state. This is done by cooling and by initiating crystallization.

Depending upon the material used for the latent-heat-storage medium, a latent heat store has a relatively high heat storage density in a defined temperature range. This enables a relatively high amount of heat energy to be stored in relatively little mass without the temperature of the latent-heat-storage medium increasing thereby. This enables virtually low-loss energy storage for a long period and with numerous repeat cycles. The latent-heat-storage medium can, for example, be organic, in particular a paraffin, and/or inorganic, for example a salt hydrate. In particular, it can be provided that the heat store comprises a crystallization-initiating unit, which is embodied to initiate crystallization of the latent-heat-storage medium when it is liquid and subcooled.

One embodiment provides that the heat store is embodied as a sorption-heat store, wherein the docking station comprises a desorption-energy-providing unit, wherein energy for desorption of a coolant in the heat store from a sorbent in the heat store can be transferred from the desorption-energy-providing unit of the docking station into the heat store via the detachable heat-conduction connection.

With a sorption-heat store, also called a thermochemical heat store, the enthalpy of vaporization and the enthalpy of bonding are used in a reversible physicochemical process. A sorption-heat store enables low-loss thermal energy storage for a long period with numerous repeat cycles.

The sorbent used can in particular be a very porous and very hygroscopic material with a very large internal surface (600-1000 m2/g). This enables heat storage densities of about 100-200 kWh/m3 to be achieved. The operating temperature depends on the material used for the sorbent, for example 40-100° C. in the case of silica gel, 130-300° C. in the case of zeolite and 280-500° C. in the case of metal hydrides.

One embodiment provides that the sorbent is zeolite, silica gel, a metal hydride or a combination thereof. Zeolite is in particular nontoxic, non-flammable and environmentally compatible. The same applies to silica gels. With a zeolite-based sorption-heat store it is, for example, possible to implement a heat storage density of 107-185 kWh/m3 in a desorption temperature range of 130–180° C.

One embodiment provides that the docking station comprises a cooling unit, which is embodied to cool the coolant in the heat store that was desorbed from the sorbent in the heat store via the detachable heat-conduction connection. In particular, the cooling unit of the docking station and the heat store, which is embodied as a sorption-heat store, can interact such that they form an adsorption chiller.

One embodiment provides that the heat-conduction connection comprises a heat pipe. The transferable power depends upon the specific heat pipe properties, in particular the capillary structure, the heat transfer agent, the vapor chamber and the operating temperature. A heat pipe can be embodied as a compact and relatively cost-efficient element with very high thermal conductivity. A heat pipe can, for example, have an operating temperature range of −40 to 275° C., a diameter of 2.5 mm, a power loss of about 20 W per cm2 infeed area and a thermal resistance of 0.02 to 0.5 kW.

One embodiment provides that the gantry comprises a heat sink, which is embodied to transfer heat from the heat store to an environment of the gantry. The heat sink can in particular enable controlled heat dissipation on the surface of the gantry. Since heat transition is dependent upon the temperature difference, the surface and the flow velocity of the cooling agent, it is favorable for the surface of the heat sink to be as large as possible. The heat sink can in particular comprise a multiplicity of cooling fins. The heat sink can in particular relieve the heat store in that a portion of the heat is transferred to the environment via the heat sink instead of being stored in the heat store. The transfer to the environment via the heat sink can in particular take place by thermal radiation and convection. The heat sink is preferably made of a material with relatively high thermal conductivity.

The portion of the heat that is transferred to the environment via the heat sink can be determined, in particular restricted, by the shape and material of the heat sink, in order, for example, to prevent an excessive increase in the room temperature in the examination room. The heat sink can in particular be embodied such that the portion of the heat that is transferred to the environment via the heat sink can be varied, for example in that the size of a surface of the heat sink is changed. To this end, the heat sink can, for example, comprise heat-sink sections that have a fan-like arrangement and can be moved relative to one another. For example, the heat transfer by the heat sink can be limited to a lesser degree on a route to the docking station and/or in a plant room in which the docking station is located than in the examination room in which the examination is performed via the computed tomography device.

One embodiment provides that the docking station is arranged in a region of a patient-support apparatus of the computed tomography device. For example, the docking station can be integrated in the patient-support apparatus of the computed tomography device, in particular in a supporting base of the patient-support apparatus. A patient support plate is arranged on the supporting base so that it can be moved relative to the supporting base. This in particular enables savings to made with respect to space and/or material that would be required for a separate docking station.

According to one embodiment, the docking station and the patient-support apparatus of the computed tomography device are connected to one another via a data transmission connection. The data transmission connection can, for example, be wired or wireless. This enables data to be transmitted between the patient-support apparatus and the docking station, in particular transmitted bidirectionally.

According to one embodiment, the docking station and the gantry of the computed tomography device can be connected, in particular are connected, detachably to one another such that a detachable data transmission connection is formed between the gantry and the docking station. The detachable data transmission connection can, for example, be wired, in particular in the form of a plug connection, or wireless, in particular in the form of near-field communication. This enables data to be transmitted between the gantry and the docking station, in particular transmitted bidirectionally.

The data can, for example, relate to the cooling of the gantry, the power supply to the gantry, projection data acquisition and/or the positioning of a patient, in particular the position of the patient support plate and/or include control commands relating to the patient-support apparatus, the docking station and/or the gantry.

The patient-support apparatus and/or the docking station can in particular be connected to a computer via a bidirectional data transmission connection. The computer can in particular be embodied to control the patient-support apparatus, the docking station, the gantry and/or the computed tomography device.

In particular, the patient-support apparatus can comprise input elements to enable a user to input control commands for the docking station. The control commands can, for example, be transmitted from the patient-support apparatus to the docking station via the data transmission connection.

For example, the patient-support apparatus can comprise an input region, in particular in the form of a touchscreen, wherein the input region is embodied in a first operating state to enable a user to input control commands for the docking station and is embodied in a second operating state to enable a user to input control commands for the patient-support apparatus. Alternation between the different operating states of the input region can, for example, be effected by a corresponding user interaction, for example in the form of a selection from a displayed context menu or by pressing a button.

At least one embodiment of the invention further relates to a method for cooling a component of a gantry of a computed tomography device, wherein the method includes:

cooling the component of the gantry, wherein heat is received in a heat store, which is integrated in the gantry, moving the gantry via a chassis relative to a docking station, connecting the gantry and the docking station detachably to one another such that a detachable coolant-exchange connection for exchanging a coolant and/or a coolant reservoir and/or a detachable heat-conduction connection for heat conduction is formed between the heat store and the docking station.

The component of the gantry can in particular be a projection-data-acquisition unit and/or comprise a projection-data-acquisition unit. The projection-data-acquisition unit can in particular comprise an X-ray source and an X-ray detector that interacts with the X-ray source. The projection-data-acquisition unit can also comprise further components, for example a rotor, wherein the X-ray source and the X-ray detector are arranged on the rotor.

According to one embodiment, the method further includes the acquisition of projection data via the projection-data-acquisition unit of the computed tomography device, wherein heat is generated by the projection-data-acquisition unit heat. The heat can, for example, be transferred to the heat store by convection and/or by heat conduction and/or by thermal radiation from the component of the gantry. In particular, the heat can be transferred on a path from the component of the gantry to the heat store comprising one or more heat exchangers. According to one embodiment, the component of the gantry is a heat exchanger.

According to one embodiment, at least a portion of the heat stored in the heat store is transferred to the docking station via the detachable heat-conduction connection.

The heat that was transferred to the docking station, can, for example, be fed to a cooling system, in particular a water-cooling system and/or a building-heating system. According to one embodiment, the heat that was transferred to the docking station can at least partially be converted into electrical energy and, for example, be fed into an electrical energy supply network.

For example, the gantry can be embodied such that it is possible to acquire projection data from a plurality of medical imaging examinations that in each case have a plurality of separate acquisition steps (scans) without the gantry being connected to the power supply with a stationary terminal.

One embodiment provides that the heat is stored in the heat store in the form of a heated coolant, wherein the heated coolant is transferred from the heat store into a coolant-store region of the docking station and/or the cooled coolant is transferred from the coolant-store region of the docking station into the heat store via the detachable coolant-exchange connection.

One embodiment provides that the heat is stored in the heat store in the form of a thermodynamic phase transition of a latent-heat-storage medium, wherein the latent-heat-storage medium in the heat store is cooled by a cooling unit of the docking station via the detachable heat-conduction connection.

One embodiment provides that the heat is received in the heat store such that the heat evaporates a coolant in the heat store, wherein the coolant is adsorbed on a sorbent in the heat store, wherein energy for desorption of the coolant from the sorption material in the heat store is transferred from the desorption-energy-providing unit of the docking station into the heat store via the detachable heat-conduction connection.

One embodiment provides that the energy for desorption of the coolant from the sorption material in the heat store desorbs the coolant from the sorption material in the heat store and/or wherein the coolant condenses in the heat store.

One embodiment provides that the coolant in the heat store that was desorbed from the sorbent in the heat store is cooled by a cooling unit of the docking station via the detachable heat-conduction connection.

The gantry's chassis can in particular be omnidirectional and/or embodied to move the gantry of the computed tomography device relative to a base. The base can, for example, be a floor of one or more rooms, in particular of an examination room, and/or a baseplate.

According to one embodiment, at least one path is defined in one or more rooms that can be used by the gantry for journeys to the docking station or away from the docking station. The traveling motion of the gantry can in particular be controlled manually by a user, for example via a traveling-motion-control unit, or take place automatically, in particular autonomously. Even when the actual traveling motion of the gantry takes place substantially autonomously, it can be provided that the traveling motion to the docking station or away from the docking station is started manually by a user, for example via a corresponding input unit that can, for example, be located on the gantry, on the docking station, on the patient-support apparatus and/or an a remote computer.

The system can in particular comprise sensors, which can be used for gantry collision avoidance and/or for gantry navigation. The sensors can be arranged on the gantry and/or in the one or more rooms. It can be further provided that the gantry stops moving and/or a sends a signal when its route is blocked and, for example, it is unable to reach the docking station. In particular, the sensors can enable an automatic, in particular autonomous, traveling motion of the gantry. In particular, the sensors can enable a relative motion of the gantry relative to the docking station such that, when the gantry approaches the docking station, the corresponding interfaces can couple to one another.

Suitable sensors and/or data processing enables, for example, it to be automatically ascertained that a gantry connected to the docking station is again ready for mobile operations. In particular, the gantry can be embodied such that it itself is able automatically determine whether it is ready for the mobile operation and/or that it is able itself automatically to ascertain whether a connection with the docking station is necessary or is still necessary. The connection with the docking station can, for example, be necessary if the gantry and/or the environment of the gantry heats up excessively and/or if the heat store of the gantry is saturated.

Depending upon the result of the ascertainment, a signal, for example in the form of a light signal, an audio signal and/or status information, can be generated and/or output. The signal can, for example, be output in the region of the gantry and/or on a remote output unit that is connected via a network and/or suitable interfaces. The output unit can in particular be a computer and/or a wearable worn by a user.

According to one embodiment, the system is embodied to carry out a method in accordance with one or more of the embodiments disclosed.

A solution according to at least one embodiment of the invention makes it possible to prevent large amounts of waste heat resulting from the operation of the computed tomography device, for example about 3-4 kilowatts, from being discharged into the examination room and thus significantly heating the examination room. In particular, the docking station can provide a cooling capacity of about 10 kilowatts, for example. Heat convection due to air flow is avoided, thus avoiding hygiene problems in cleanroom examination rooms, in particular operating rooms, and enabling higher hygiene standards to be maintained.

The chassis enables flexible, independent and omnidirectional motion of the gantry in the room. The gantry can be parked in a space-saving manner and/or configured and/or positioned differently to enable better access to the patient. The same gantry can be used in succession in several rooms. There is no need for complex ceiling designs and/or room designs for the movable guidance of, for example, terminals and/or cables. Furthermore, there is no need for a rail system in the floor.

In particular, when using a heat store in which thermal energy can be stored with a higher energy density than in water, the space requirement for the heat store in the gantry is relatively low.

In particular, the heat store can be embodied such that rapid cooling of components of the gantry, for example within a few minutes, is enabled. As a result, the computed tomography device can carry out a plurality of acquisition steps (scans) rapidly in sequence, in particular without any delay due to cool-down times for the X-ray source or other heated components of the gantry.

Furthermore, the gantry, in particular the heat store of the gantry and the docking station, can interact to cool components of the gantry such that no condensed water forms on the surface of the gantry or that any condensed water that does form on a surface of the gantry evaporates or is collected and fed to a collecting tank relatively quickly, for example in less than 12 hours. For quicker evaporation of the condensed water, it is in particular possible for a fan and/or a heater to be provided. The fan and/or the heater can, for example, be arranged on the gantry and/or on the docking station and/or separate from the gantry and the docking station in a room. As a result, it is possible to prevent the formation of a biofilm on the surface of the gantry as a nutrient medium for bacteria that can be whirled up.

In the context of the invention, features described with respect to different embodiments of the invention and/or different claim categories (method, use, apparatus, system, arrangement etc.) can be combined to form further embodiments of the invention. For example, a claim relating to an apparatus can also be developed with features described or claimed in conjunction with a method and vice versa. Herein, functional features of a method can be implemented by correspondingly embodied material components. In addition to the embodiments of the invention expressly described in this application, numerous further embodiments of the invention are conceivable at which the person skilled in the art can arrive without departing from the scope of the invention in so far as it is defined by the claims.

The use of the indefinite article "a" or "an" does not preclude the possibility of the feature in question also being present on a multiple basis. The use of the term "comprise" does not preclude the possibility of the terms being linked by the term "comprise" being identical. For example, the gantry comprises the gantry. The use of the term "unit" does not preclude the possibility of the subject matter to which the term "unit" relates comprising a plurality of components that are spatially separated from one another.

FIG. 1 shows a system 1 with a heat store W embodied as a coolant store and a detachable coolant-exchange connection VK between the gantry 20 and the docking station D.

The system 1 comprises the gantry 20 of the computed tomography device 2 and the docking station D. The gantry 20 comprises the chassis F and the heat store W. The gantry 20 can be moved via the chassis F relative to the docking station D and relative to the floor N.

The gantry 20 and the docking station D can be connected, in particular are connected, detachably to one another such that a detachable coolant-exchange connection VK for exchanging a coolant KT, KH is formed between the heat store W and the docking station D. The docking station D comprises a coolant-store region DK. A heated coolant KH can be transferred from the heat store W into the coolant-store region DK of the docking station D via the detachable coolant-exchange connection VK. A cooled coolant KT is transferred from the coolant-store region DK of the docking station D into the heat store W via the detachable coolant-exchange connection VK.

The heat is stored in the heat store W in the form of a heated coolant KH. The heated coolant KH is pumped from the heat store W and into the coolant-store region DK, in particular into the coolant-storage reservoir DK1 via the detachable coolant-exchange connection VK. Then, the coolant KT cooled in the docking station D is pumped out of the coolant-store region DK, in particular out of the coolant-storage reservoir DK2, into the empty heat store W.

The gantry 20 can then be detached from the docking station 20 and, for example, acquire projection data. Meanwhile, the previously heated coolant KH is cooled in the docking station D. When the previously cooled coolant KT has been heated up again in the heat store W, the gantry 20 returns to the docking station D in order to form the detachable coolant-exchange connection VK and to exchange the coolant KT, KH via the detachable coolant-exchange connection VK. This operating cycle can be repeated many times.

Figure 2:
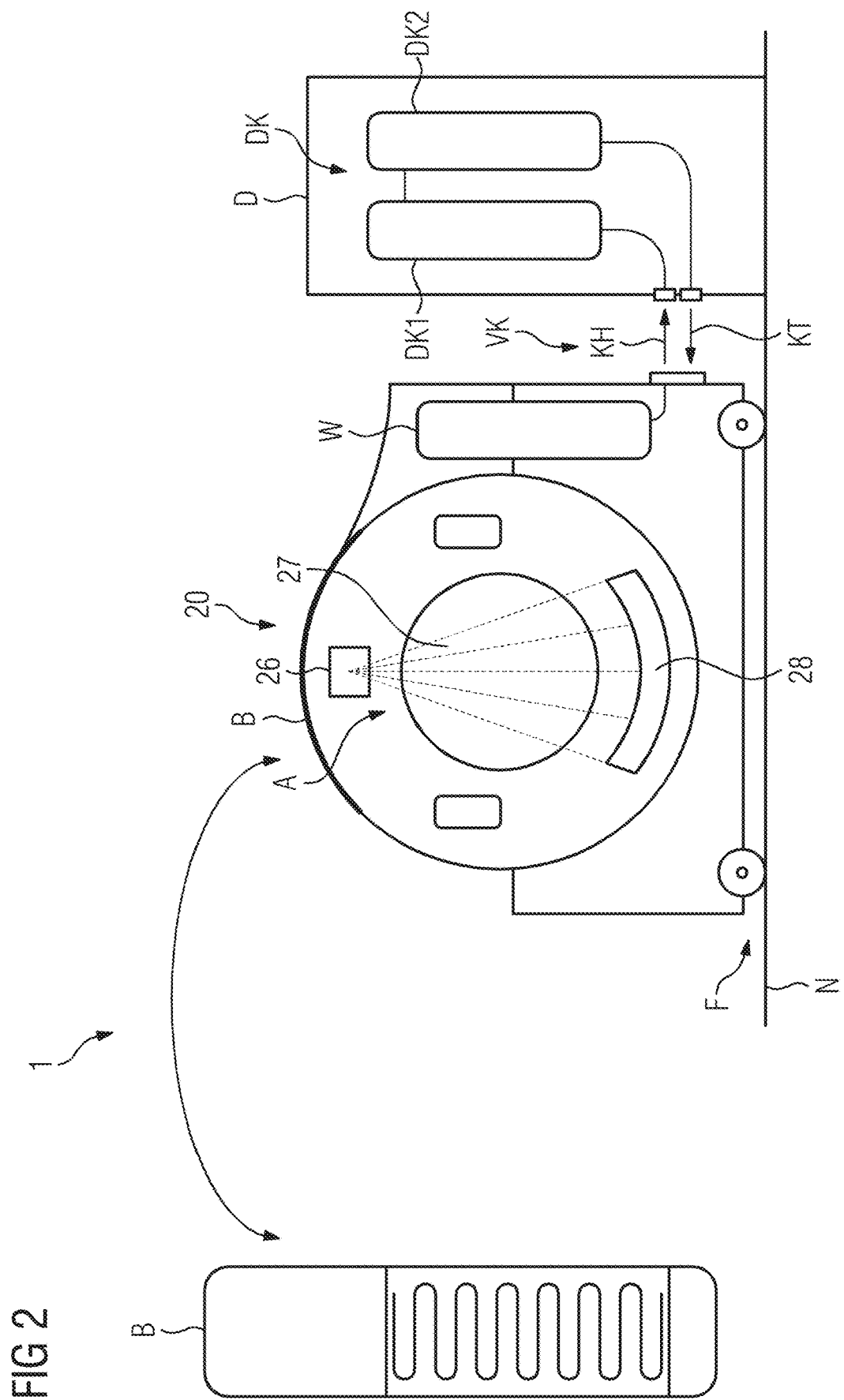

FIG. 2 shows a system 1 with a heat store W, which is embodied as a coolant store, a detachable coolant-exchange connection VK between the gantry 20 and the docking station D and a heat sink B. The gantry 20 comprises the heat sink B, which is embodied to transfer heat from the heat store W to an environment of the gantry 20.

Figure 3:
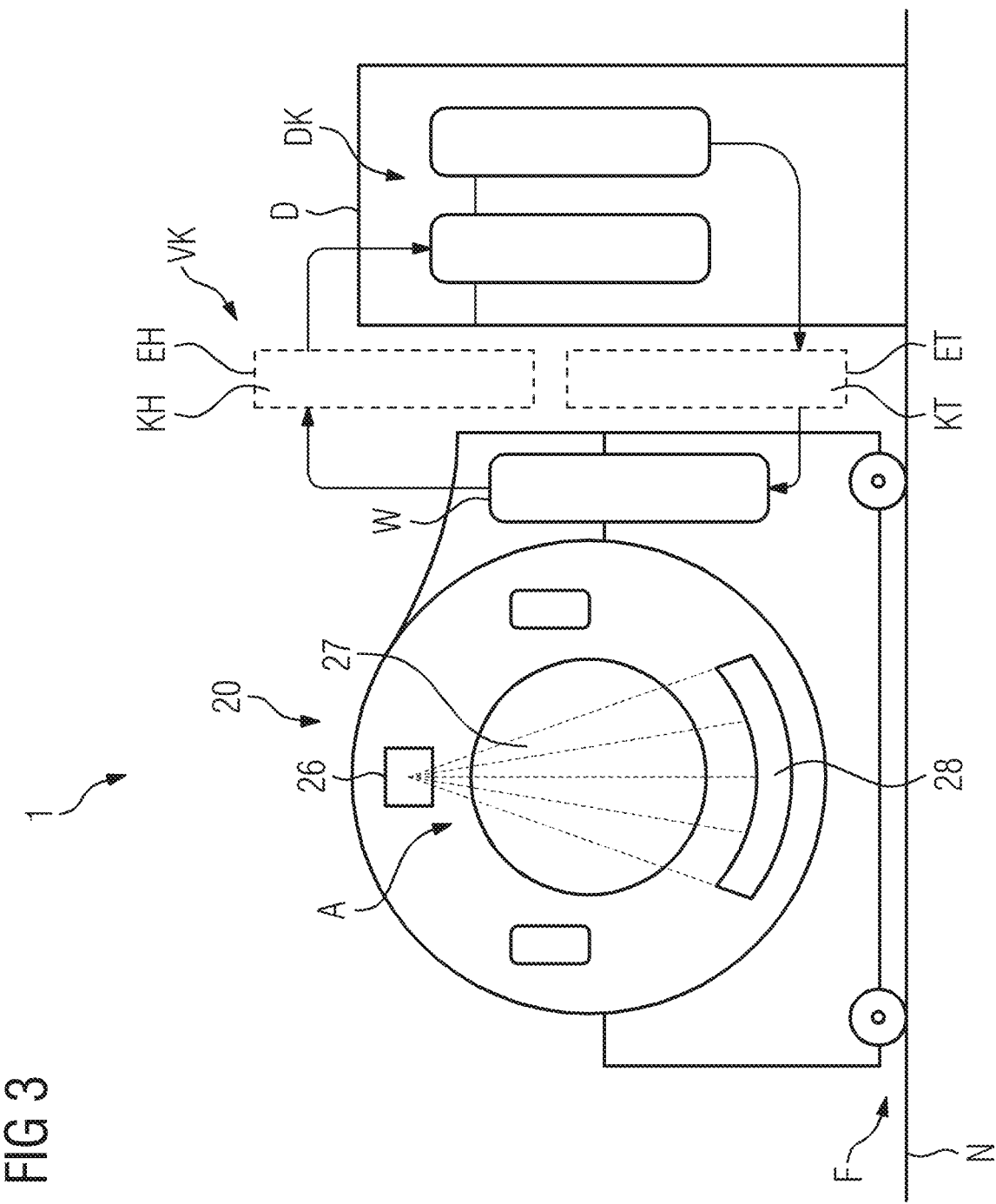

FIG. 3 shows a system 1 with a heat store W, which is embodied as a coolant store, a detachable coolant-exchange connection VK between the gantry 20 and the docking station D for exchanging a coolant KT, KH and a coolant reservoir ET, EH.

The coolant reservoir EH in which the heated coolant KH is located is separated from the heat store W and from the gantry 20 and received in the coolant-store region DK of the docking station D. The coolant reservoir ET in which the cooled coolant KT is located is separated from the coolant-store region DK and from the docking station D and received in the heat store W.

Figure 4:
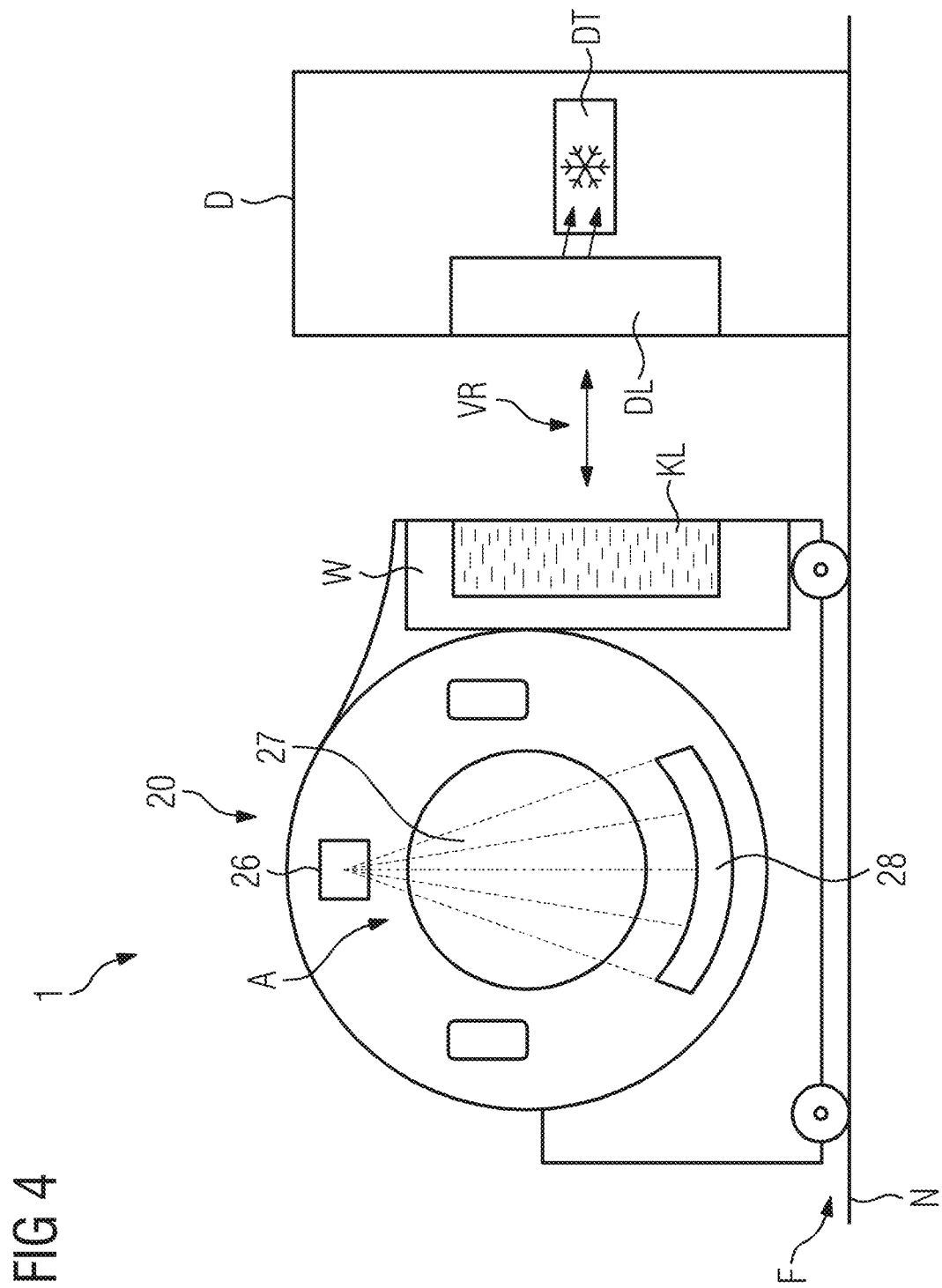

FIG. 4 shows a system 1 with a heat store W embodied as a latent heat store and a detachable heat-conduction connection VR. The latent-heat-storage medium KL is located in a capsule in the heat store W. The docking station D comprises a cooling unit DT, which is embodied to cool a latent-heat-storage medium KL in the heat store W via the detachable heat-conduction connection VR. The heat in the heat store W is stored in the form of a thermodynamic phase transition of a latent-heat-storage medium KL in the heat store W. The cooling unit DT of the docking station D cools, in particular subcools, the latent-heat-storage medium KL in the heat store W via the detachable heat-conduction connection VR. Triggering the crystallization of the latent-heat-storage medium KL enables the thermodynamic phase transition to be undone so that heat can be stored again in the form of the thermodynamic phase transition of a latent-heat-storage medium KL in the heat store W. The cooling unit DT of the docking station D can, for example, be embodied for active cooling and/or for passive cooling. In particular, the cooling unit DT can comprise cooling fins for passive cooling which are embodied on a surface of the docking station D.

Figure 5:
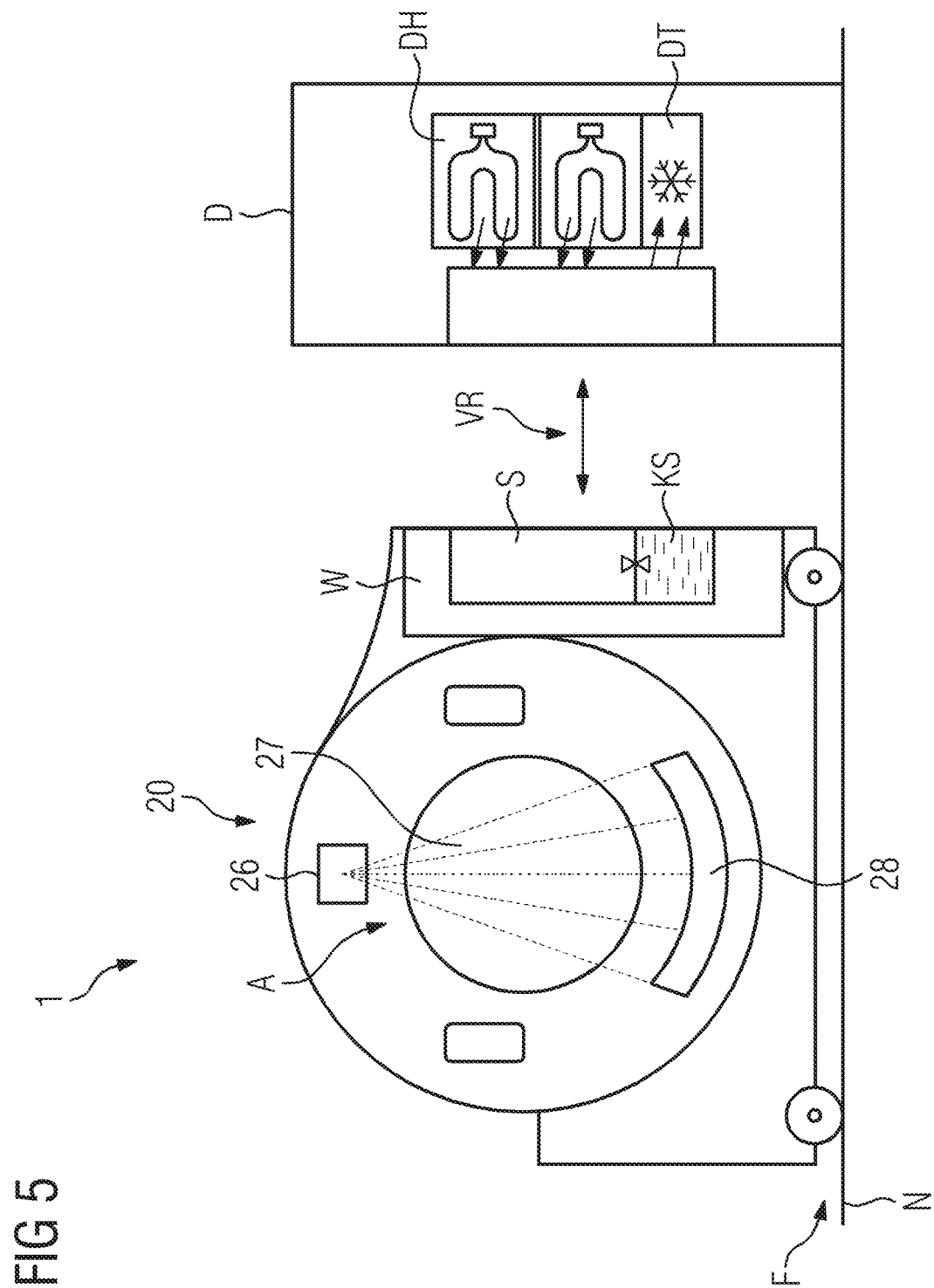

FIG. 5 shows a system 1 with a heat store W embodied as a sorption-heat store and a detachable heat-conduction connection VR. The docking station D comprises a desorption-energy-providing unit DH, wherein energy for desorption of a coolant KS in the heat store W from a sorbent S in the heat store W can be transferred from the desorption-energy-providing unit DH of the docking station D into the heat store W via the detachable heat-conduction connection VR.

The docking station D comprises a cooling unit DT, which is embodied to cool the coolant KS in the heat store W that was desorbed from the sorbent S in the heat store W, via the detachable heat-conduction connection VR. The sorbent S is for example zeolite. The coolant KS is for example water.

The heat is received into the heat store W such that the heat evaporates a coolant KS in the heat store W. The coolant KS is adsorbed on the sorbent S in the heat store W. The energy for desorption of the coolant KS from the sorption material S in the heat store W is transferred from the desorption-energy-providing unit DH of the docking station D into the heat store W via the detachable heat-conduction connection VR. The energy for desorption of the coolant KS from the sorption material S in the heat store W desorbs the coolant KS from the sorption material S in the heat store. The coolant KS is then condensed in the heat store W.

The coolant KS in the heat store W that was desorbed from the sorbent S in the heat store W is cooled by a cooling unit DT of the docking station D via the detachable heat-conduction connection VR. Hence, the detachable heat-conduction connection VR includes a plurality of paths.

A first path of the heat-conduction connection VR transfers energy for desorption of the coolant KS from the sorption material S in the heat store W from the desorption-energy-providing unit DH of the docking station D into the heat store W, in particular onto the sorption material S. A second path of the heat-conduction connection VR cools the coolant KS in the heat store W that was desorbed from the sorbent S in the heat store W by a cooling unit DT of the docking station D, in particular to assist the condensation of the coolant KS. The reception of heat into the heat store W enables the previously condensed coolant KS to be evaporated again and adsorbed on the sorbent S. This operating cycle can be repeated many times.

In particular, it can be provided that the heat store W comprises two regions which in each case comprise a partial quantity of the sorption material S and a partial quantity of the coolant KS. If the coolant KS is alternatively evaporated and adsorbed in a region of the heat store W, while the coolant KS is desorbed and condensed in the other region of the heat store W, the gantry 20 can be cooled continuously.

In the example embodiment shown in FIG. 5, the desorption-energy-providing unit DH is integrated in the docking station D in the form of heating elements and provides thermal energy for desorption of the coolant KS in the heat store W from the sorbent S in the heat store W. Alternatively thereto, the desorption-energy-providing unit DH can be a source of electrical energy, wherein the electrical energy is transferred to the gantry 20 via a detachable electrical connection. The gantry 20 can, for example, comprise heating elements in the region of the sorbent S in the heat store W in which the electrical energy is converted into thermal energy for desorption of the coolant KS in the heat store W from the sorbent S in the heat store W.

The gantry 20 can, for example, comprise cooling elements in the region of the heat store W in order to assist the condensation of the coolant KS. The cooling elements can in particular be operated with electrical energy which is provided by the docking station D and transferred to the gantry 20 via a detachable electrical connection.

Figure 6:
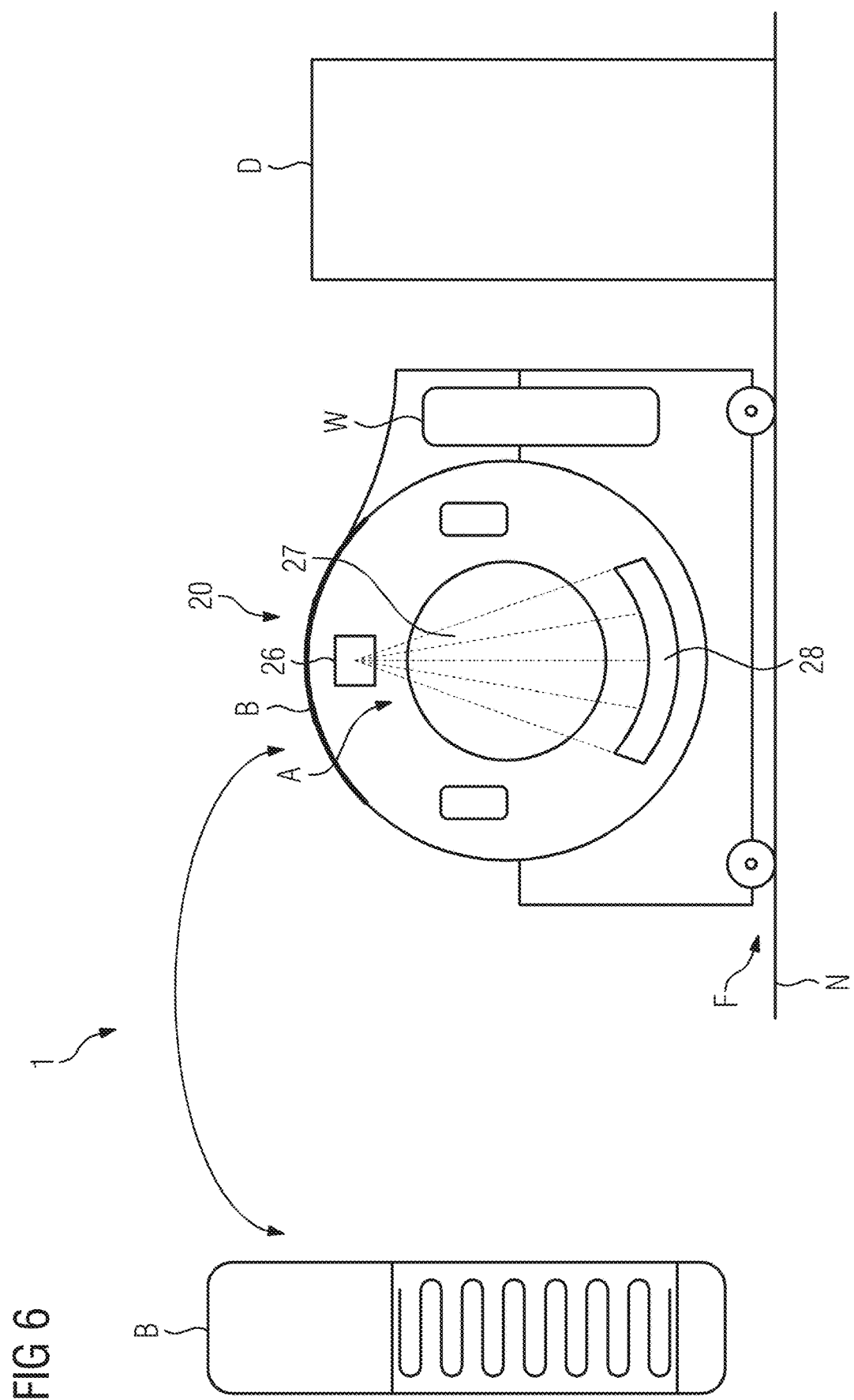

FIG. 6 shows a system 1 with a heat store W and a heat sink B, wherein the gantry 20 and the docking station D are not connected via a detachable coolant-exchange connection and also not connected via a detachable heat-conduction connection. In particular, the heat sink B and the heat store W can interact such that the regeneration of the heat store W is substantially effected by the transmission of the heat from the heat store W to an environment of the gantry 20 via the heat sink B.

Figure 7:
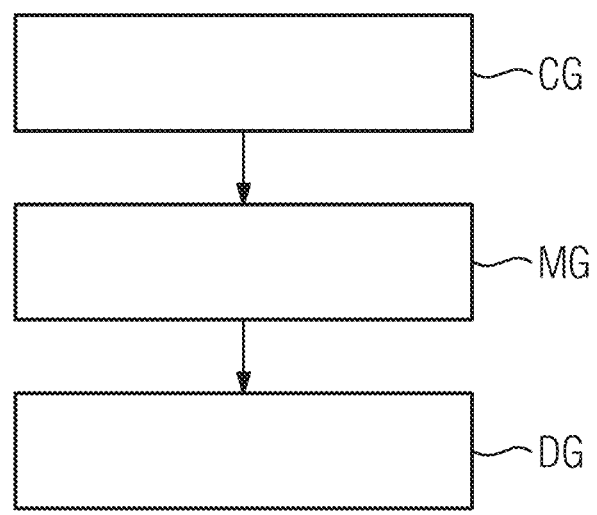

FIG. 7 shows a sequence diagram of a method for cooling a component A of a gantry 20 of a computed tomography device 2, wherein the method includes the following steps: cooling CG the component A of the gantry 20, wherein heat is received in a heat store W which is integrated in the gantry 20, moving MG the gantry 20 via a chassis F relative to a docking station D, connecting DG the gantry 20 and the docking station D detachably to one another such that a detachable coolant-exchange connection VK for exchanging a coolant KT, KH in the heat store W and/or a detachable heat-conduction connection VR is formed between the heat store W and the docking station D.

Figure 8:
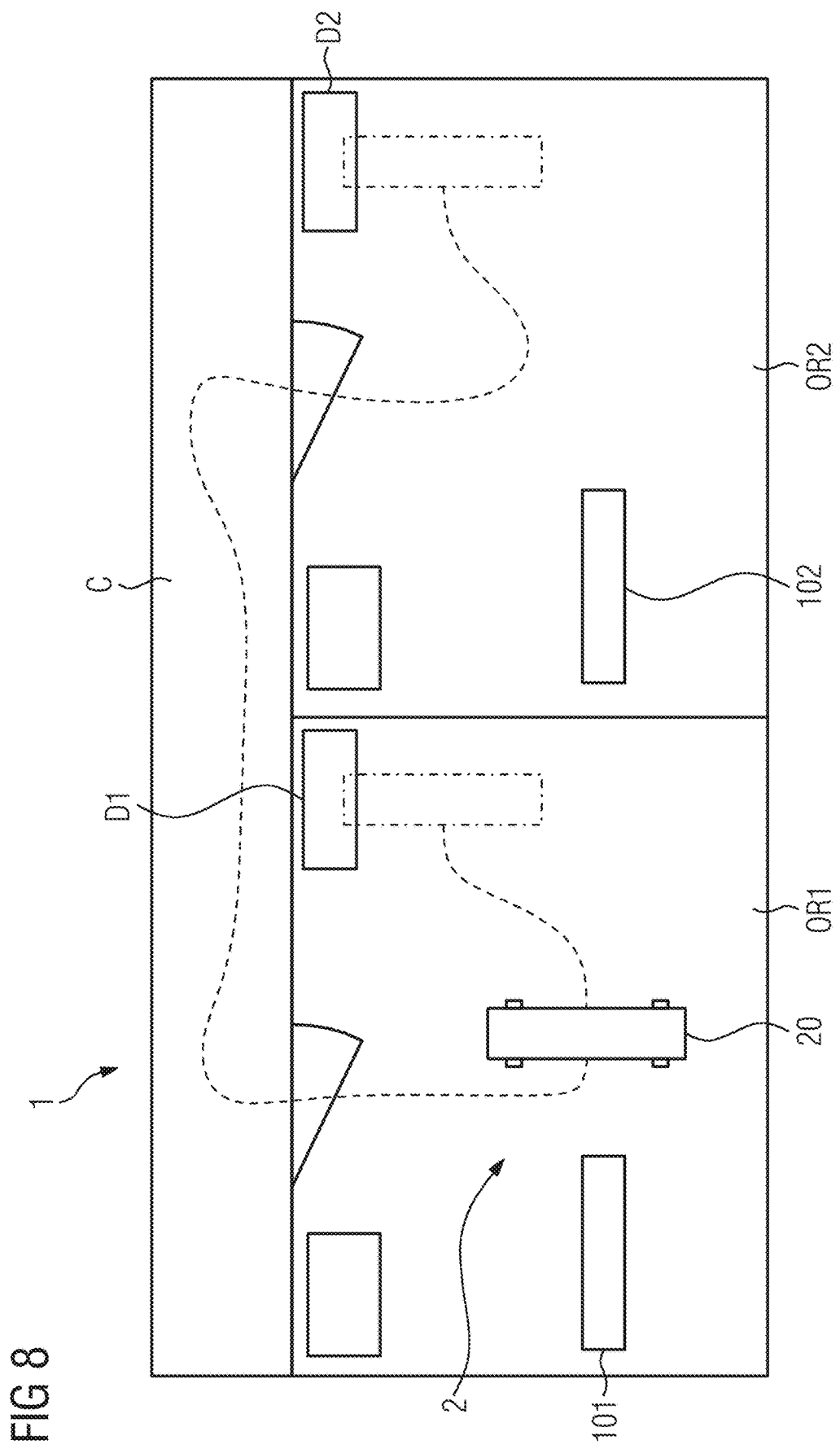

FIG. 8 shows a system 1 with a plurality of docking stations D1 and D2, which are arranged in different rooms OR1 and OR2, which can for example be operating rooms. The patient-support apparatus 101 is located in OR1. The patient-support apparatus 102 is located in room OR2. Rooms OR1 and OR2 are connected via a corridor C. The dashed lines identify paths on which the gantry 20 can travel to the docking stations D1 and D2.

The gantry 20 is detachably connected to each of the docking stations D1 and D2 such that a detachable coolant-exchange connection VK for exchanging a coolant KT, KH and/or a detachable heat-conduction connection VR for heat conduction is formed between the heat store W and the docking station D1 or D2. Thus it is possible to regenerate the heat store W in each of the rooms OR1 and OR2 using the corresponding docking station D1 or D2.

Figure 9:
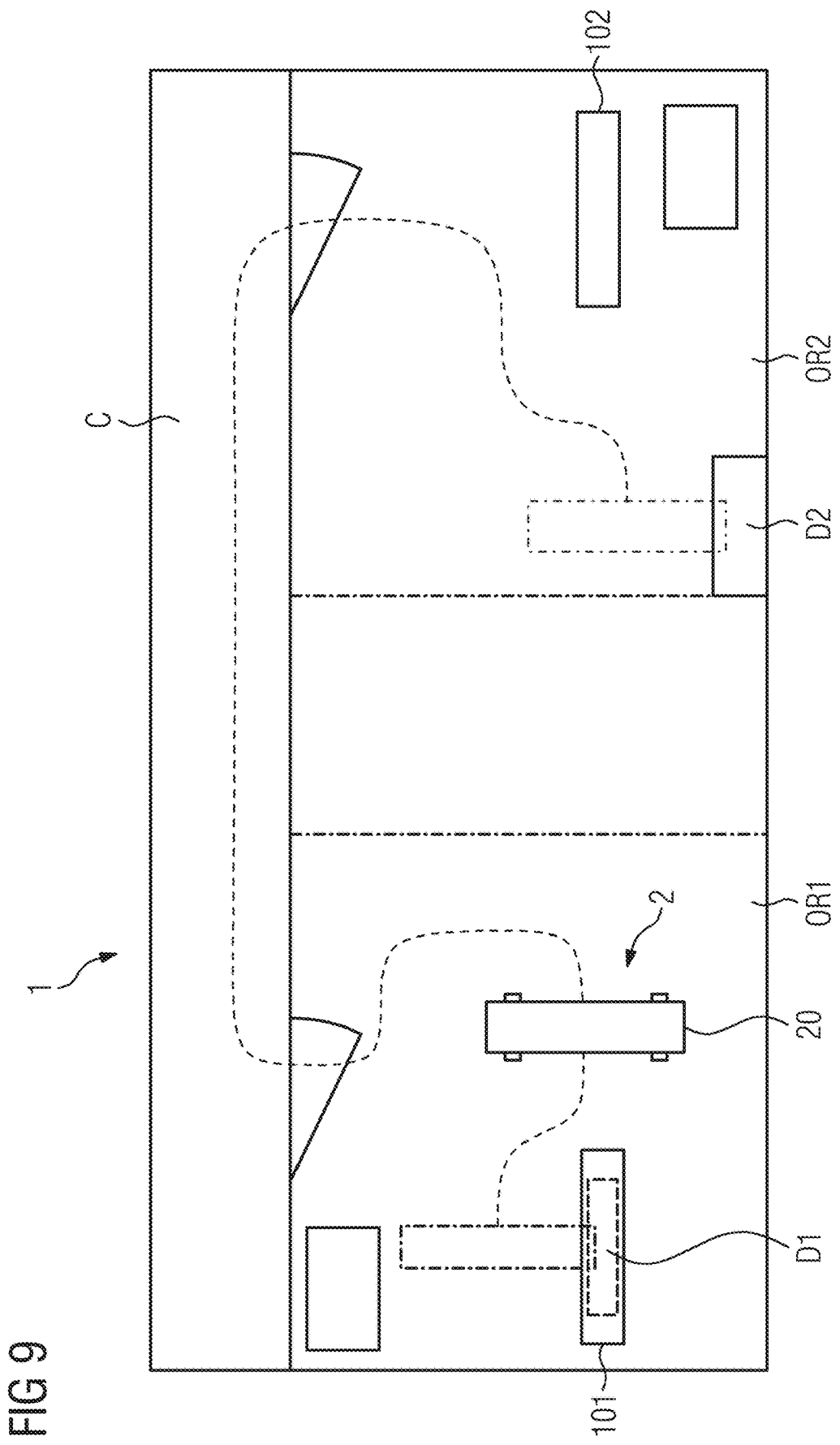

FIG. 9 shows a system 1 with a plurality of docking stations, which are arranged in different rooms OR1 and OR2, wherein the docking station D1 is arranged in a region of the patient-support apparatus 101 of the computed tomography device 2, in particular integrated in the patient-support apparatus 101.

Figure 10:
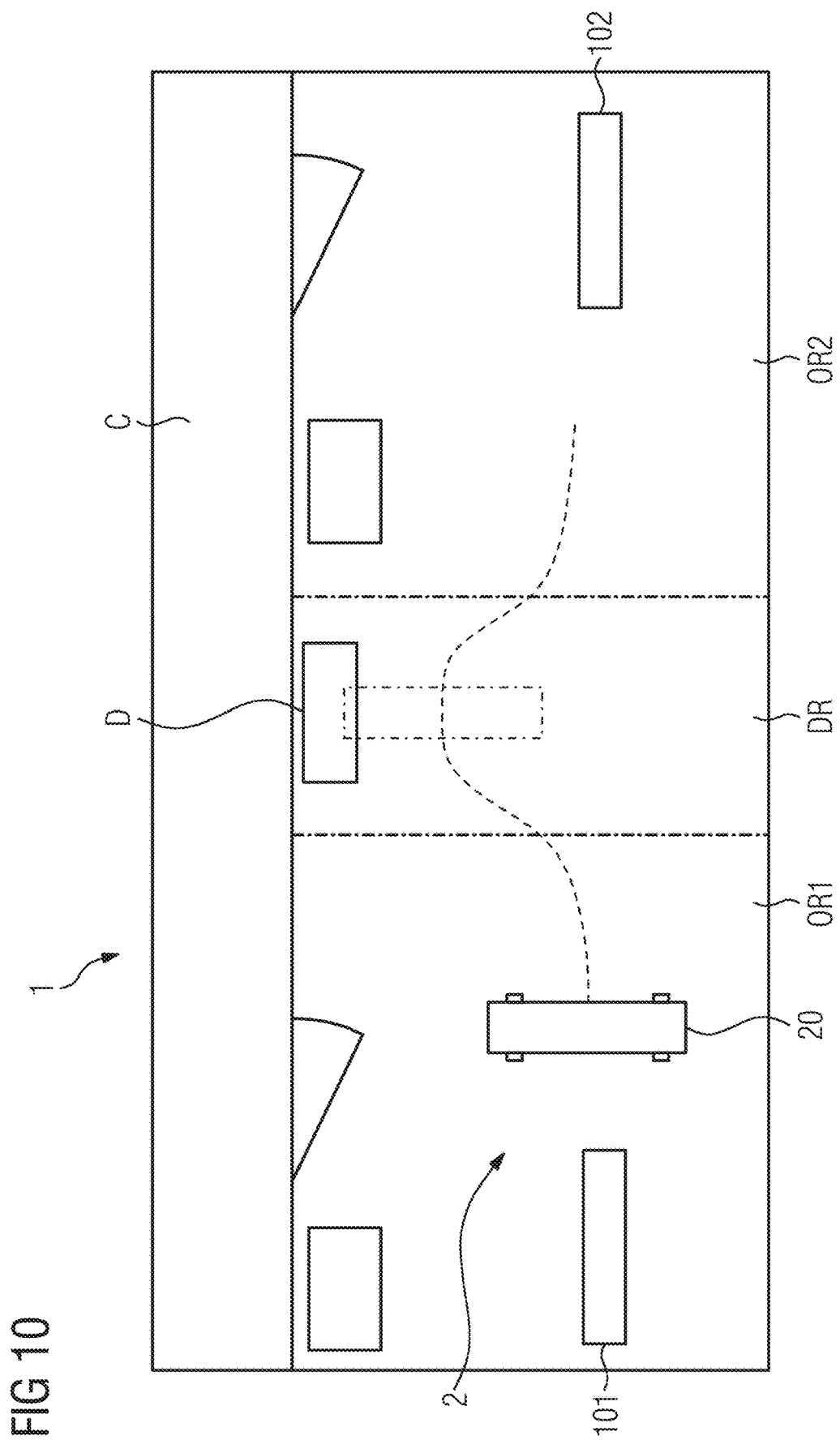

FIG. 10 shows a system 1 with a docking station D, which is arranged in a docking-station room DR, which is located between the two rooms OR1 and OR2. In the example embodiment shown in FIG. 10, the docking-station room DR can be reached directly from each of the two rooms OR1 and OR2, in particular without a detour via the corridor C.

Figure 11:
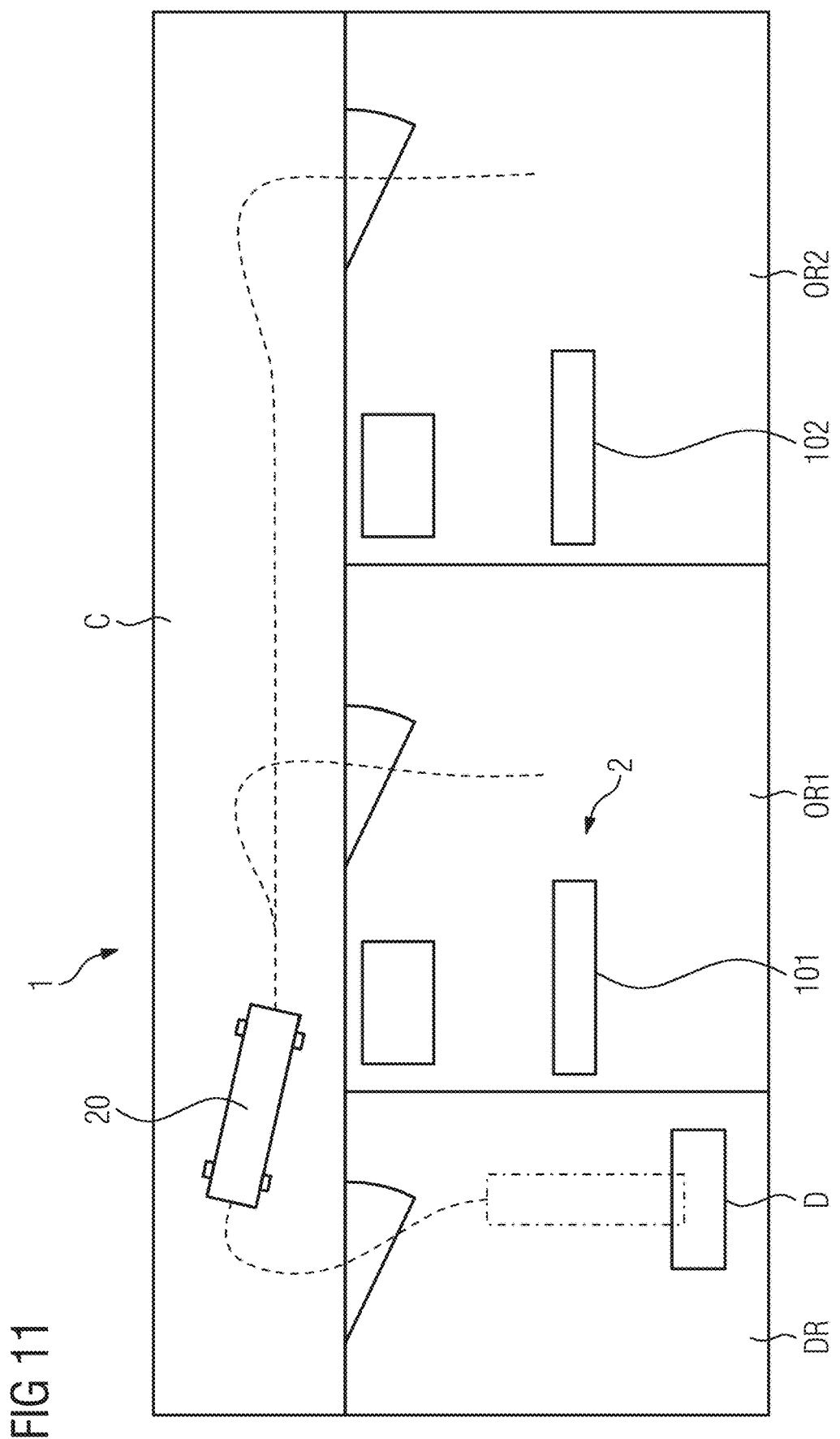

FIG. 11 shows a system 1 with a docking station D, which is arranged in a docking-station room DR embodied as a separate plant room that can only be reached via the corridor C. In particular, the gantry 20 can travel to the docking-station room DR as soon as the reserves of electrical energy run low and/or the heat store W is saturated. When the regeneration of the heat store W and/or charging of a rechargeable electrical energy store of the gantry 20 is completed, the gantry 20 can travel autonomously into one of the rooms OR1 and OR2. The navigation of the gantry 20 between the docking-station room DR and the rooms OR1 and OR2 can in particular be implemented in advance, for example based on defined paths and substantially autonomously by the gantry 20.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system comprising:
a gantry of a computed tomography device, the gantry including a chassis and a heat store; and
a docking station, wherein
the gantry is configured to move relative to the docking station via the chassis,
the gantry and the docking station are configured to be detachably connected to form a detachable coolant-exchange connection for exchanging a coolant reservoir between the heat store and the docking station,
the coolant reservoir includes a heated coolant or a cooled coolant, and
the coolant reservoir is exchanged between the heat store and the docking station by at least one of
transferring the coolant reservoir including the heated coolant from the heat store to the docking station, or
transferring the coolant reservoir including the cooled coolant from the docking station to the heat store.

2. The system of claim 1, wherein the docking station is arranged on, or in a region of, a patient-support apparatus of the computed tomography device.

3. The system of claim 1, wherein the gantry is configured to move independent of the docking station via the chassis.

4. The system of claim 1, wherein the chassis is an omnidirectional chassis.

5. The system of claim 1, wherein the chassis is a wheel-based chassis.

6. The system of claim 5, wherein the wheel-based chassis is an omnidirectional chassis or a rail-based chassis.

7. The system of claim 1, wherein the chassis is a rail-based chassis.

8. The system of claim 1, further comprising:
a rail system; and wherein
the chassis is configured to move along the rail system.

9. The system of claim 1, wherein the gantry includes a heat sink configured to transfer heat from the heat store to an environment of the gantry.

10. A system, comprising:
a gantry of a computed tomography device, the gantry including a chassis and a heat store; and
a docking station, wherein
the gantry is configured to move relative to the docking station via the chassis,
the gantry and the docking station are configured to be detachably connected to form a detachable coolant-exchange connection for exchanging at least one of a coolant or a coolant reservoir between the heat store and the docking station, and
the gantry includes a heat sink configured to transfer heat from the heat store to an environment of the gantry.

11. The system of claim 10, wherein
the heat store is a coolant store,
the docking station includes a coolant-store region, and
the coolant is exchanged between the heat store and the docking station by at least one of
transferring a heated coolant from the heat store to the coolant-store region, or
transferring a cooled coolant from the coolant-store region to the heat store.

12. A system comprising:
a gantry of a computed tomography device, the gantry including a chassis and a heat store, the heat store configured to hold a coolant reservoir;
a docking station configured to hold the coolant reservoir, wherein
the gantry is configured to move relative to the docking station via the chassis, and
the gantry and the docking station are configured to be detachably connected to form a detachable coolant-exchange connection; and
a coolant reservoir exchanging apparatus configured to transfer the coolant reservoir between the heat store and the docking station.

13. The system of claim 12, wherein
the coolant reservoir is configured to hold a cooled coolant or a heated coolant, and
the coolant reservoir exchanging apparatus is configured to at least one of
transfer the coolant reservoir holding the cooled coolant from the docking station to the heat store, or
transfer the coolant reservoir holding the heated coolant from the heat store to the docking station.

14. The system of claim 12, wherein the gantry includes a heat sink configured to transfer heat from the heat store to an environment of the gantry.

15. The system of claim 12, wherein the docking station is arranged on, or in a region of, a patient-support apparatus of the computed tomography device.

16. The system of claim 12, wherein the gantry is configured to move independent of the docking station via the chassis.

17. The system of claim 12, wherein the chassis is an omnidirectional chassis.

18. The system of claim 12, wherein the chassis is a wheel-based chassis.

19. The system of claim 18, wherein the wheel-based chassis is an omnidirectional chassis or a rail-based chassis.

20. The system of claim 12, wherein the chassis is a rail-based chassis.

21. The system of claim 12, further comprising:
a rail system; and wherein
the chassis is configured to move along the rail system.

22. A method for cooling a component of a gantry of a computed tomography device, the method comprising:
cooling the component of the gantry, wherein heat is received in a heat store in the gantry;

moving the gantry relative to a docking station via a chassis;
connecting the gantry and the docking station to form a detachable coolant-exchange connection between the heat store and the docking station, the detachable coolant-exchange connection being for exchanging a coolant reservoir between the heat store and the docking station; and
exchanging the coolant reservoir between the heat store and the docking station; wherein
   the coolant reservoir is configured to hold a cooled coolant or a heated coolant, and
   the exchanging includes at least one of
      transferring the coolant reservoir holding the cooled coolant from the docking station to the heat store, or
      transferring the coolant reservoir holding the heated coolant from the heat store to the docking station.

23. The method of claim 22, wherein
the heat is stored in the heat store as the heated coolant,
the detachable coolant-exchange connection is also for exchanging a coolant between the heat store and the docking station, and
the exchanging includes at least one of
   transferring the heated coolant from the heat store to a coolant-store region of the docking station, or
   transferring a cooled coolant from the coolant-store region of the docking station to the heat store.

24. The method of claim 22, wherein the moving moves the gantry independent of the docking station via the chassis.

25. The method of claim 22, wherein the chassis is an omnidirectional chassis.

26. The method of claim 22, wherein the chassis is a wheel-based chassis.

27. The method of claim 26, wherein the wheel-based chassis is an omnidirectional chassis or a rail-based chassis.

28. The method of claim 22, wherein the chassis is a rail-based chassis.

29. The method of claim 22, wherein the moving moves the gantry relative to the docking station along a rail system via the chassis.

30. The method of claim 22, further comprising:
transferring heat from the heat store to an environment of the gantry via a heat sink.

* * * * *